United States Patent [19]

Stavroff et al.

[11] Patent Number: 5,866,145
[45] Date of Patent: Feb. 2, 1999

[54] BODY POLISHER

[75] Inventors: Vera Stavroff; Neil Goeren, both of New Albany, Ohio

[73] Assignee: Bath & Body Works, Inc., Columbus, Ohio

[21] Appl. No.: 789,767

[22] Filed: Jan. 28, 1997

[51] Int. Cl.$^6$ ........................................................ A61K 7/00

[52] U.S. Cl. ............................................ 424/401; 514/887

[58] Field of Search ................................ 424/401, 78.03; 514/887

[56] References Cited

U.S. PATENT DOCUMENTS

| | | | |
|---|---|---|---|
| 4,389,418 | 6/1983 | Burton | 424/365 |
| 4,943,432 | 7/1990 | Biener | 424/647 |

*Primary Examiner*—Thurman K. Page
*Assistant Examiner*—D. Faulkner
*Attorney, Agent, or Firm*—Colucci & Umans

[57] ABSTRACT

A body polisher and method of using the body polisher as a skin treatment, includes a two phase composition containing Dead Sea salt and emollient. The emollient is advantageously silicone oil and is present in about 32.67% by weight. About 66.66% by weight Sea salt is provided, the remainder being fragrance.

4 Claims, No Drawings

BODY POLISHER

FIELD AND BACKGROUND OF THE INVENTION

The present invention relates in general to lotions for rubbing on the body, and in particular, to a new and useful body polisher which contains a moisturizing oil in which sea salt is suspended.

Compositions for smoothing and moisturizing the skin have long been known.

A water-in-oil composition is disclosed in U.S. Pat. No. 5,262,087, which contains selected ingredients to emulsify the skin without leaving the skin with an oily feeling. The composition includes dimethylpolysiloxane, a silicone oil.

A silicone oil-in-water emulsifier is also disclosed in U.S. Pat. No. 5,300,286.

Other skin treating compositions containing silicon components are disclosed in U.S. Pat. Nos. 5,480,637 and 5,478,555.

It is also known to use various salts in bath water. Epson salt has long been known as a therapeutic composition for use in bath water. A recipe which was circulated on the Internet on May 5, 1996, also calls for the use of Epson salt with sea salt and vegetable glycerin plus a few drops of essential oils to produce a useful bath water additive. The use of salts dissolved in bath water does not contemplate rubbing a lotion with salts directly on the skin, however.

SUMMARY OF THE INVENTION

The present invention comprises a body polisher which contains, as its essential ingredients, sea salt, in particular Dead Sea salt, known by the trade name AFRO salt, plus an emollient and skin conditioner, in particular, that in the form of silicone oils such as dimethicone.

In addition, small quantities of fragrance are added.

It has been found that this composition helps smooth, exfoliate and moisturize the skin.

Accordingly, an object of the present invention is to provide a bodyrub or body polisher which contains a fluid emollient and sea salt suspended in the emollient. The invention also includes a method of treating the skin comprising rubbing on to the skin a suspension of sea salt in emollient, in particular, silicone oil emollient.

DESCRIPTION OF THE PREFERRED EMBODIMENT

The preferred composition of the present invention uses a relatively large amount of sea salt, in particular, AFRO salt in an amount of about 66.66%, with an emollient and skin conditioner, in particular, Dimethicone DC 345 in an amount of about 32.67%. In addition, about 0.66% fragrance is included in the composition. All percentages in this disclosure are by weight.

Dimethicone is a dimethyl polysiloxane, that is, a silicone oil consisting of dimethylsiloxane polymers.

Genuine Dead Sea salt has been found to be particularly useful for the present invention. Salt, having the chemical formula NaCl and an appropriate crystalline size, other than Dead Sea salt, may also be effective although not as useful in exfoliating and smoothing the skin. The fact that the salt remains in a suspension gives the composition a gritty yet pleasant feel when applied to the skin. Since salt is soluble in water, the rub can also be rinsed away leaving only a residual layer of oil which acts as a skin moisturizer.

Although the preferred proportions of salt, moisturizer and fragrance have been disclosed above, the composition may contain from about 50 to about 80 percent salt, from about 20 to about 50 percent emollient, preferably emollient which is water dispersible, if not water soluble, and 0.1 to 2.0 percent fragrance.

It is also advantageous that the body polisher of the present application be supplied in a two phase condition. The aroma is also an important component, although not essential. The aroma is conjunction with the feel of the composition as it is being applied has been found to have a therapeutic effect on an individual which, in addition to the physical improvement in the condition of the skin, is accompanied by a psychological improvement caused by the combination of a pleasant scent and a tingly tactile sensation on the skin.

While a specific embodiment of the invention has been shown and described in detail to illustrate the application of the principles of the invention, it will be understood that the invention may be embodied otherwise without departing from such principles.

What is claimed is:

1. A method of treating skin comprising:
   rubbing onto the skin a body polisher lotion comprising a mixture of sodium chloride salt and oil emollient, the salt being a gritty solid component in suspension in the oil emollient so that the lotion is a two phase lotion which feels gritty to the touch and which exfoliates and moisturizes the skin when the lotion is rubbed onto the skin;
   continuing the rubbing until the skin is exfoliated to allow the oil emollient to penetrate into the skin; and
   after the step of continuing, at least partly rinsing the body polisher lotion off the skin with water.

2. A method according to claim 1, wherein the oil emollient comprises silicone oil, the body polisher including fragrance in an amount of 0.1 to 2.0% by weight.

3. A method according to claim 1, when the oil emollient comprises dimethylpolysiloxane.

4. A method according to claim 1, including about 66% by weight salt, about 33% by weight emollient and about 1% by weight fragrance.

* * * * *